(12) United States Patent
Tanaka

(10) Patent No.: US 6,607,272 B1
(45) Date of Patent: *Aug. 19, 2003

(54) RETINAL BLOOD FLOW MEASURING APPARATUS USING A LASER BEAM

(75) Inventor: Shinya Tanaka, Tokyo (JP)

(73) Assignee: Canon Kabushiki Kaisha, Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/710,494

(22) Filed: Sep. 18, 1996

Related U.S. Application Data

(63) Continuation of application No. 08/264,499, filed on Jun. 23, 1994, now abandoned.

(30) Foreign Application Priority Data

Jun. 28, 1993 (JP) ............................................. 5-182004

(51) Int. Cl.[7] .............................. A61B 3/14; A61B 3/10
(52) U.S. Cl. .......................... 351/206; 351/221; 396/18
(58) Field of Search ................................. 351/205, 206, 351/208, 209, 211, 213, 214, 221; 354/62; 128/691, 667, 745; 396/18

(56) References Cited

U.S. PATENT DOCUMENTS

| | | | | |
|---|---|---|---|---|
| 4,856,891 A | * | 8/1989 | Pflibsen et al. | 351/206 X |
| 4,952,050 A | * | 8/1990 | Aizu et al. | 351/221 |
| 5,240,006 A | * | 8/1993 | Fujii et al. | 128/691 X |
| 5,455,644 A | * | 10/1995 | Yazawa et al. | 351/206 |

* cited by examiner

*Primary Examiner*—Huy Mai
(74) *Attorney, Agent, or Firm*—Fitzpatrick, Cella, Harper & Scinto

(57) ABSTRACT

A retinal blood flow measuring apparatus has an irradiation system for spot-applying a laser beam for measurement onto a blood flow in the fundus of an eye to be examined, a light receiving device for receiving the reflected light of the laser beam for measurement from the fundus of the eye, the blood flow state of the fundus of the eye being measured from the light reception signal of the light receiving device, and a prescribing member for prescribing the position of the reflected light from the fundus of the eye in the direction of depth of the fundus of the eye.

19 Claims, 5 Drawing Sheets

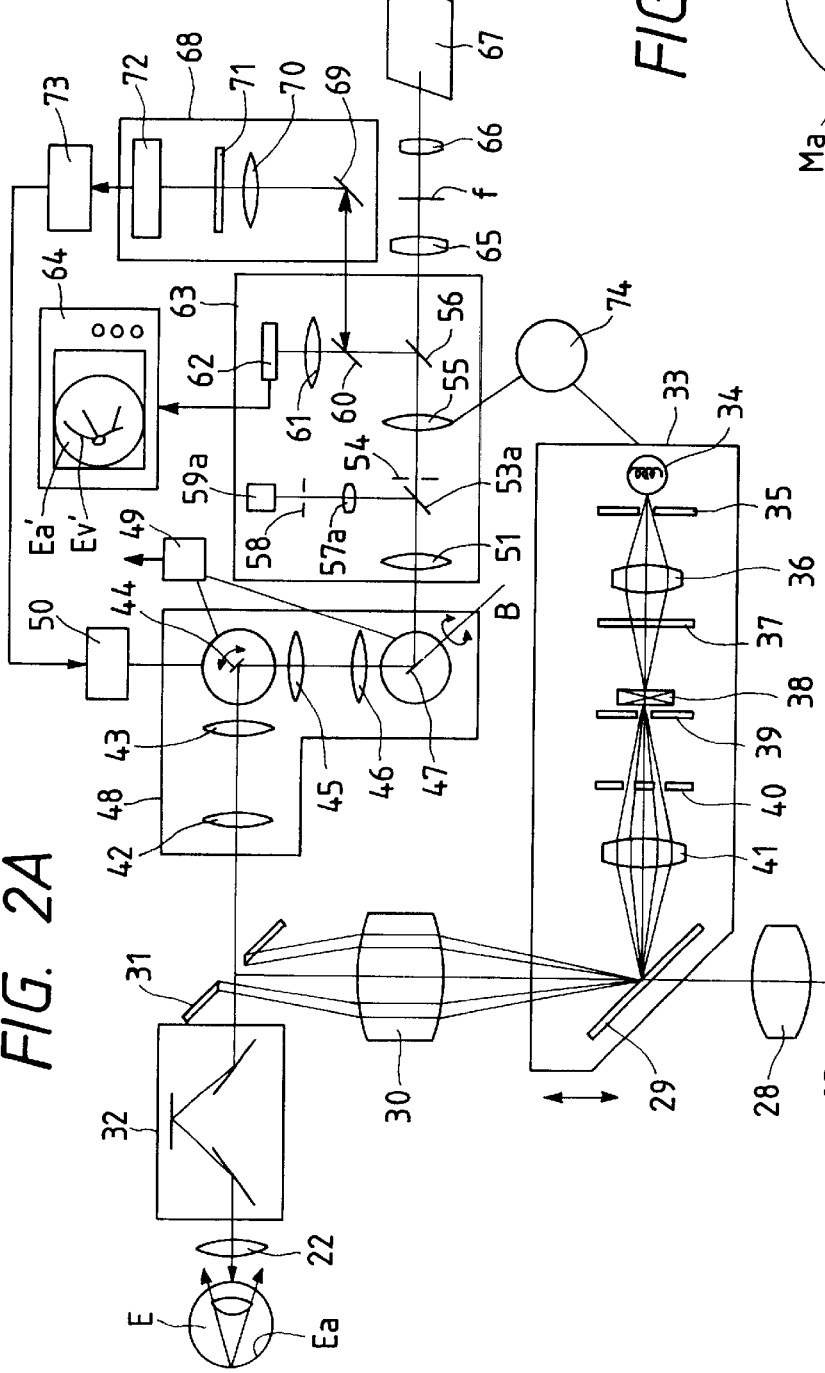
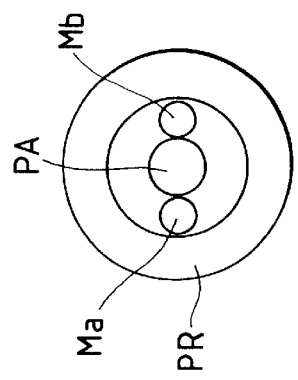
FIG. 2A
FIG. 2B

RETINAL BLOOD FLOW MEASURING APPARATUS USING A LASER BEAM

This application is a continuation of application Ser. No. 08/264,499 filed Jun. 23, 1994, now abandoned.

BACKGROUND OF THE INVENTION

1. Field of the Invention

This invention relates to a retinal blood flow velocimeter for measuring a blood flow in a blood vessel on the fundus of an eye to be examined.

2. Related Background Art

FIG. 1A of the accompanying drawings shows a retinal blood flow velocimeter according to the prior art in which a slit lamp generally used for ophthalmic diagnosis and treatment has been reconstructed. An illumination optical system is disposed on an optical path k1, and an illuminating white light from an observation light source 1 is reflected by an apertured mirror 2 and illuminates a blood vessel Ev on the fundus Ea of an eye E to be examined, through a slit 3, a lens 4 and a contact lens 5 which offsets the refractive power of the cornea of the eye E to be examined and makes the fundus Ea of the eye observable. A coherent light source such as a He—Ne laser 6 for emitting a mesuring or probing beam (for measurement) is disposed behind the apertured mirror 2, and the mesuring or probing beam from the coherent light source 6 (for measurement) passes through an opening at the center of the apertured mirror 2, is made coaxial with the illumination light from the observation light source 1 and irradiates the fundus Ea of the eye at a point.

Light scattered and reflected by fundus Ea passes through the objective lenses 7a and 7b of a light receiving optical system for stereoscopic observation disposed on optical paths k2 and k3 forming an angle α' therebetween, is reflected by mirrors 8a, 8b and mirrors 9a, 9b, and is observed as the image of the fundus of the eye by an examiner through eyepieces 10a and 10b, and the examiner selects a region to be measured while looking into the eyepieces 10a and 10b and observing the fundus Ea of the eye.

FIG. 1B of the accompanying drawings shows the image of the fundus of the eye observed by the examiner. When the blood vessel Ev to be observed in an area illuminated by the illuminating light is registered with a scale Sc prepared in advance on the focal plane of the eyepiece 10a or 10b, the probing beam from the light source 6 for measurement is registered with the blood vessel Ev, and the region to be measured is determined by a beam spot PS of the probing beam from the light source 6 for measurement. At this time, the light of scattered by the vessel on the fundus Ea of the eye is detected by photomultipliers 12a and 12b through fibers 11a and 11b.

This detected signal includes a beat signal component created by a signal component which has been Doppler-shifted by a blood flow flowing through the vessel Ev and a reference component which has been reflected by the wall of the blood vessel interfering with each other, and by frequency-analyzing this beat signal, the velocity of the blood flow in the blood vessel Ev can be found.

FIG. 1C of the accompanying drawings shows an example of the result of the frequency analysis of the detected signal detected by the photomultipliers. In FIG. 1C, the abscissa represents the frequency $\Delta f$, and the ordinate represents the spectrum power $\Delta S$ thereof. The relation among the maximum value $\Delta f\text{max}$ of the frequency, the wave number vector $Ki$ of the incident beam, the wave number vector $Ks$ of the received beam of light and the velocity vector $v$ of the blood flow can be written as $$\Delta f\text{max} = (Ks - Ki) \cdot v. \tag{1}$$

Accordingly, when equation (1) is modified by the use of two maximum values $\Delta f\text{max1}$ and $\Delta f\text{max2}$ calculated from the detected signals of each photomultiplier 12a and 12b, the wavelength $\lambda$ of the laser beam, the refractive index n of the region to be measured, the angle α between the detecting optical axes K2 and K3 in the eye, and the angle β formed between the plane formed by the light receiving optical axes K2 and K3 in the eye, the maximum velocity Vmax of the blood flow can be written as $$V\text{max} = \{\lambda/(n\alpha)\} \cdot |\Delta f\text{max1} - \Delta f\text{max2}|/\cos \beta. \tag{2}$$

By measuring from two directions in this manner, the contribution of the incident beam in the direction of incidence is offset and the blood flow in any region on the fundus Ea of the eye can be measured, without the certain directions of the incident beam and detecting beam in the eye.

It is necessary in order to measure the true velocity of the blood flow that β must be known in equation (2). In the example of the prior art, the design is such that the whole light receiving optical system is rotated or an image rotator is disposed in the light receiving optical system to thereby make the line of intersection A optically coincident with the velocity vector $v$ or the direction of the vessel.

However, in the above-described example of the prior art, visible light is projected onto the eye to be examined to effect measurement and observation and therefore, it is necessary to dilate the pupil of the eye to be examined, and a mydriatic must be dropped in the eye. The mydriatic is a kind of anesthetic and its influence upon the blood flow in the fundus of the eye cannot be neglected. In order to avoid using this type of drug, invisible light is useful for all light sources. But the following problems will arise.

Firstly, in the case of the observation of the fundus of the eye by invisible light such as near infrared light, the focusing on the fundus of the eye becomes more difficult than that in the case if the observation is made by visible light. The infrared light reaches the deep part of the retina and the difference in reflectance between the hemoglobin in the blood and the melanin of the retinal pigment epitherium (RPE) decreases and therefore, the contrast of the image of the fundus of the eye is remarkably reduced.

Secondly, as shown in FIG. 1D of the accompanying drawings, where measurement is effected by the use of visible light, particularly red light which is of high reflectance on the fundus of the eye, most of the probing beam IL is reflected as the reflected light RL from red blood cell in the vessel. However, by near infrared light being used as the probing beam, the reflection and absorption by red blood cell are reduced. Therefore, the light is transmitted through the blood flow on the retina R and reaches the choroid RC beyond the Retinal pigment epitherium. A lot of blood vessels SV exist in the choroid RC, and the scattered light DL there mixes with the reflected light RL. Then a sensor receives this mixture-signal, which reduces the accuracy of the mesurement, and this gives rise to the problem that highly accurate measurement cannot be accomplished.

SUMMARY OF THE INVENTION

In view of the above-noted problems, it is a first object of the present invention to provide a retinal blood flow velocimeter in which blood flow velocity information from a desired depth can be accurately obtained even when infrared light is used.

It is a second object of the present invention to provide a retinal blood flow velocimeter in which an examiner can sufficiently grasp the depth information of a region to be measured even when infrared light is used.

Other objects of the present invention will become apparent from the following detailed description of an embodiment of the invention.

BRIEF DESCRIPTION OF THE DRAWINGS

FIG. 2A shows the construction of a first embodiment of the present invention.

FIG. 2B illustrates the disposition relations among the images of a ring slit, a pair of small mirrors and an aperture on the pupil of an eye to be examined.

DETAILED DESCRIPTION OF THE PREFERRED EMBODIMENTS

Figure 1A:
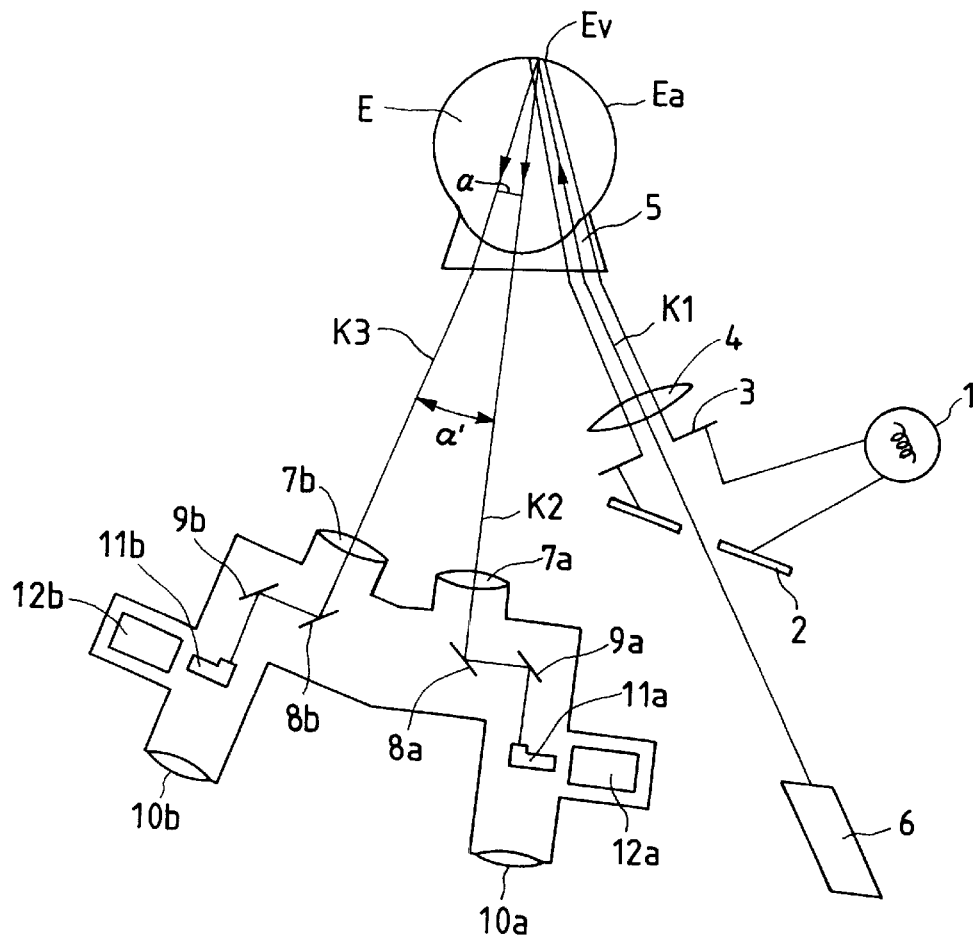
FIG. 1A shows the construction of an example of the prior art.
Figure 1B:
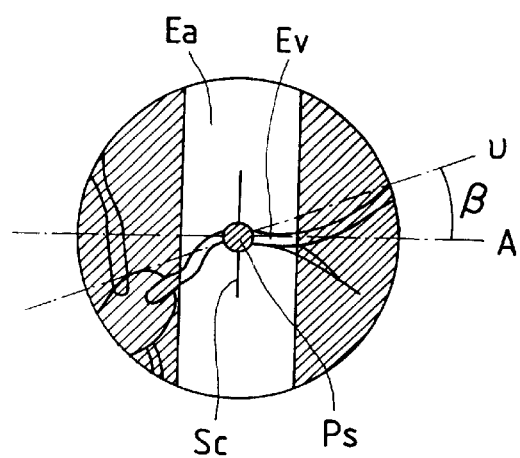
FIG. 1B is an illustration of the view of the fundus of an eye observed by an examiner.
Figure 1C:
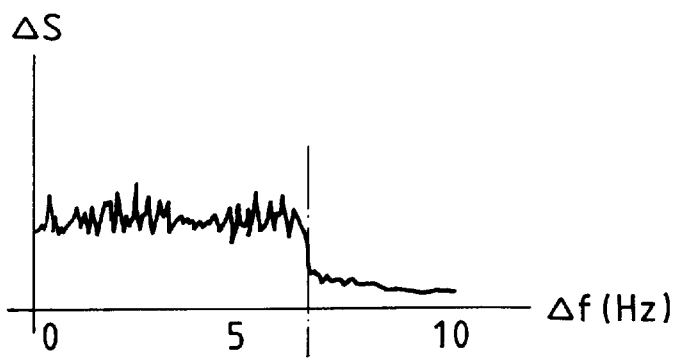
FIG. 1C is a frequency distribution graph of the output of a photomultiplier.
Figure 1D:
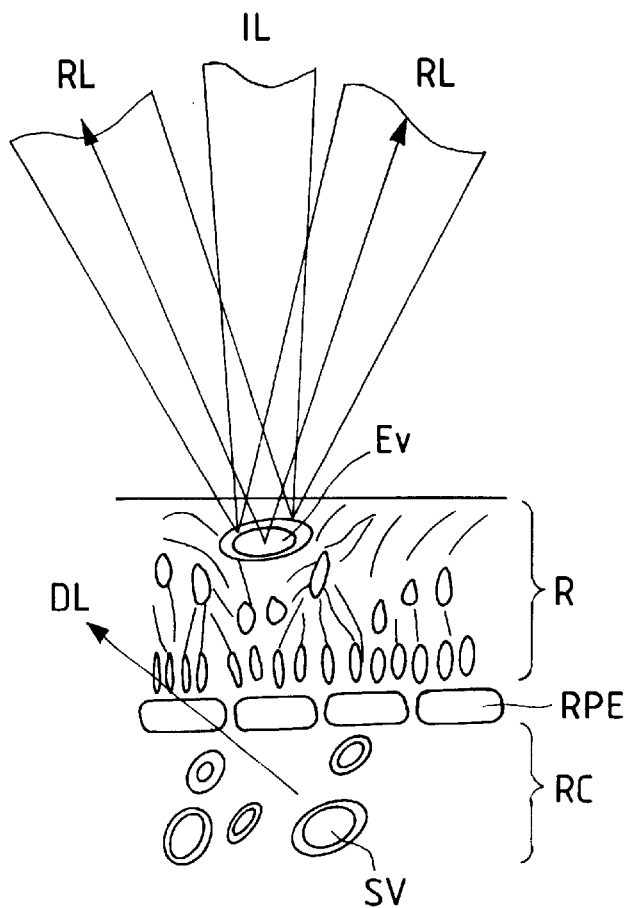
FIG. 1D is a cross-sectional view of the fundus of the eye.

The invention will hereinafter be described in detail with respect to an embodiment thereof shown in FIGS. 2A to 6.

FIG. 2A shows the construction of a first embodiment utilizing the type of a retinal camera. On an optical path leading from an illuminating light source 21 including a tungsten lamp or the like emitting near infrared light to an objective lens 22, there are disposed a visible light cut filter 23, a condenser lens 24, a mirror 25, a field lens 26, a ring slit 27 having a ring-shaped opening, a relay lens 28, a partially reflecting mirror 29, a relay lens 30, an apertured mirror 31 having an opening at the center thereof, and an image rotator 32.

On an optical path behind the partially reflecting mirror 29, there is provided a focus indicator 33 for indicating the focused state on the fundus Ea of an eye E to be examined, and on an optical path leading from a near infrared light source 34 to the partially reflecting mirror 29, there are disposed a rectangular aperture stop 35 having a rectangular opening, a condenser lens 36, a filter 37, a split prism 38, an opening index mask 39 having an opening, a light beam shaping stop 40 having two openings, and a lens 41.

Further, on an optical path behind the apertured mirror 31, there are disposed lenses 42, 43, a galvanometric mirror 44, lenses 45, 46 and a galvanometric mirror 47, by which an image stabilizer 48 is constituted. The galvanometric mirrors 44 and 47 are made conjugate with the apertured mirror 31 by the lenses 42, 43, 45 and 46, the galvanometric mirror 44 has a rotational axis in a direction perpendicular to the plane of the drawing sheet of FIG. 2A, and the galvanometric mirror 47 has a rotational axis B in the plane of the drawing sheet orthogonal to the rotational axis of the galvanometric mirror 44, and is rotated by the operation of a Joy stick 49. Driving means 50 is connected to the galvanometric mirror 44.

On an optical path in the direction of reflection of the galvanometric mirror 47, a focusing lens 51 and a pair of small mirrors 53a, 53b which are in conjugate relationship with the pupil of the eye to be examined are provided symmetrically with respect to the optical path (the small mirror 53b is not shown in FIG. 2A). Behind the small mirrors 53a, 53b, there are disposed an aperture 54 conjugate with the pupil, a focusing lens 55 and a dichroic mirror 56, and on optical paths in the directions of a reflection of the pair of small mirrors 53a and 53b, there are disposed lenses 57a, 57b (of which the lens 57b is not shown), a small hole 58 disposed on the optical path which is in conjugate relationship with the fundus Ea of the eye E to be examined, and photomultipliers 59a, 59b (of which the photomultiplier 59b is not shown). Thus, in FIG. 2A, only the members on the optical axis of the small mirror 53a are shown in order to avoid duplication. Also, on an optical path in the direction of reflection of the dichroic mirror 56, there are disposed a half mirror 60, a lens 61 and a television camera 62, by which an observation optical system 63 is constituted, and the output of the television camera 62 is connected to a monochromatic television monitor 64.

On an optical path behind the dichroic mirror 56, there are disposed lenses 65 and 66 for projecting a beam of probing beam, and a laser source 67 for measurement. Further, a blood vessel detecting system 68 is provided on an optical path in the direction of refection of the half mirror 60, and there are disposed a mirror 69, a lens 70, a filter 71 and a CCD line sensor 72 with an image intensifier. The output of the CCD line sensor 72 is connected to the driving means 50 by way of a controller 73. The focusing lens 55 and the focus indicator 33 are movable along the optical axis by a focus knob 74.

The images of the ring slit 27, the pair of small mirrors 53a and 53b and the aperture 54 on the pupil of the eye E to be examined are a ring image PR, small mirror images Ma and Mb and an aperture image PA, respectively, as shown in FIG. 2B.

Illuminating light emitted from the illuminating light source 21 becomes near infrared light via the visible light cut filter 23, is imaged by the ring slit 27 via the condenser lens 24 and the mirror 25, passes through the partially reflecting mirror 29 and the relay lens 30, is once imaged by the apertured mirror 31, passes through the image rotator 32, is again imaged as the ring image PR shown in FIG. 2B on the pupil of the eye E to be examined by the objective lens 22, and substantially uniformly illuminates the fundus Ea of the eye E to be examined. The field lens 26 is for efficiently directing the beam of light into the eye E to be examined.

The beam of reflected light from the fundus Ea of the eye passes again through the objective lens 22 and the image rotator 32, passes through the opening in the apertured mirror 31, is reflected by the galvanometric mirror 47 via the lenses 42, 43, the galvanometric mirror 44 and the lenses 45, 46 in the image stabilizer 48, passes through the focusing lens 51, the aperture 54 and the focusing lens 55 in the observation optical system 63, is reflected by the dichroic mirror 56 and is divided in two directions by the half mirror 60. The beam of light transmitted through the half mirror 60 passes through the lens 61 and is imaged as an eye fundus image Ea' on the television camera 62, and the eye fundus image is displayed on the television monitor 64. The examiner effects the alignment of the apparatus and the selection of the region to be measured while observing the television monitor 64.

On the other hand, the beam of light reflected by the half mirror 60 is imaged on the CCD line sensor 72 with an image intensifier as a blood vessel image Ev' more enlarged than the eye fundus image Ea' picked up by the television camera 62, via the mirror 69, the lens 70 and the filter 71 in the blood vessel detecting system 68.

The beam of light from the laser source 67 for measurement is transmitted through the lens 66, the lens 65 and the dichroic mirror 56 of the observation optical system 63, passes through the focusing lens 55, the aperture 54 and the focusing lens 51, passes through the image stabilizer 48, passes through the opening in the apertured mirror 31, the image rotator 32 and the objective lens 22, is made into the aperture image PA on the pupil, and illuminates the fundus Ea of the eye E to be examined in the fashion of a point. The beam of reflected light from the fundus Ea of the eye returns along the same optical path, and a part of it is reflected in two directions by the pair of small mirrors 53a and 53b.

The light scattered or reflected by fundus which is not reflected by the pair of small mirrors 53a and 53b is a light derived from the aperture image PA on the pupil, as shown in FIG. 2B, and it passes through the aperture 54 and the focusing lens 55, is reflected by the dichroic mirror 56, passes through the half mirror 60 and the lens 61, and is imaged as a beam spot PS including a small circle together with the eye fundus image Ea' by the illuminating light source 21, by the television camera 62, and the spot image PS is displayed on the television monitor 64.

On the other hand, the light reflected by the pair of small mirrors 53a and 53b are light derived as mirror images Ma and Mb on the pupil, and they pass through the lenses 57a, 57b and the small hole 58 and are received by the photomultipliers 59a and 59b. The measurement angle a shown in FIG. 1A which is subtended by the mirror images Ma and Mb is found, and the light detection signal is analyzed by the use of the Doppler measurement principle as in the prior art to thereby find the blood flow velocity in the retinal vessel of the fundus Ea.

At this time, the reflected light on the fundus Ea of the eye from the laser source 67 for measurement is reflected by the half mirror 60 and enters the blood vessel detecting system 68, but the wavelength of the laser source 67 is intercepted in the filter 71 disposed on this side of the CCD line sensor 72 and therefore, the beam of light from the laser source 67 for measurement does not reach the CCD line sensor 72, and the CCD line sensor 72 picks up only the blood vessel eye fundus image Ev' by the illuminating light source 21. The light reception signal of the CCD line sensor 72 is outputted to the controller 73, in which the amount of movement of the blood vessel image Ev' in the direction of arrangement of the elements of the CCD line sensor 72 is calculated, whereby the fine movement of the fixation of the eye E to be examined in this direction is monitored.

The focus indicator 33 has the function of projecting onto the eye E to be examined the indicator when the examiner effects focusing. The beam of light emitted from the near infrared light source 34 passes through the rectangular aperture stop 35, whereafter it passes through the condenser lens 36, the filter 37 and the split prism 38 and is separated in two directions, and is once imaged at mask 39. Since the split prism 38 divides the opening in the mask 39 into two, the two beams of light separated by the split prism 38 pass through two different openings in the light beam shaping stop 40, are again imaged on the partially reflecting mirror 29 by the lens 41 and are reflected, and pass through the relay lens 30, the apertured mirror 31, the image rotator 32 and the objective lens 22, and are projected onto the fundus Ea of the eye together with the light from the illuminating light source 21.

Figure 3:
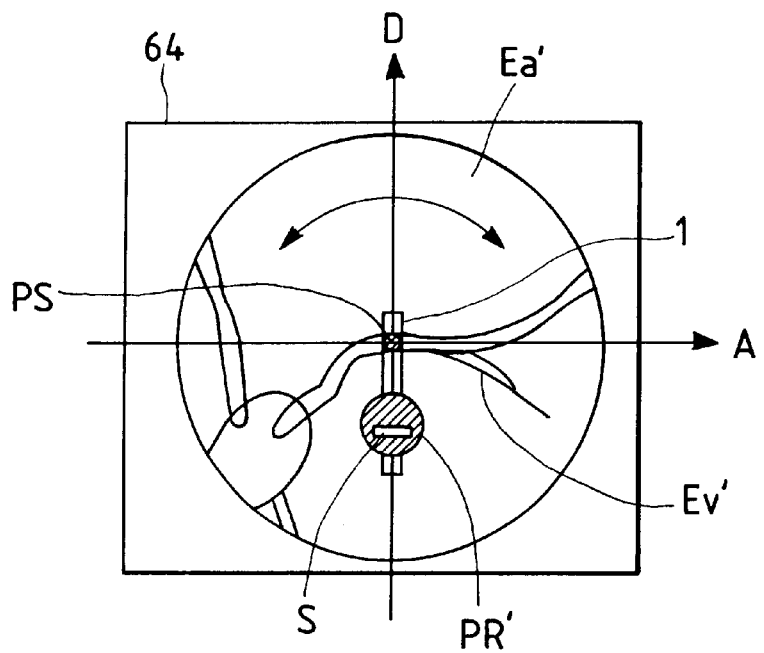
FIG. 3 is an illustration of the image of the fundus of the eye on a television monitor.

The beam of reflected light from the fundus Ea of the eye E to be examined returns along the same optical path, passes through the opening in the apertured mirror 31 and the optical members of the image stabilizer 48, passes through the focusing lens 51, the aperture 54 and the focusing lens 55, is reflected by the dichroic mirror 56, passes through the half mirror 60 and the lens 61, and is formed as an index mark image S on the television camera 62, and this image, together with the eye fundus image Ea' and the spot image PS, is displayed on the television monitor 64 as shown in FIG. 3.

Figure 4:
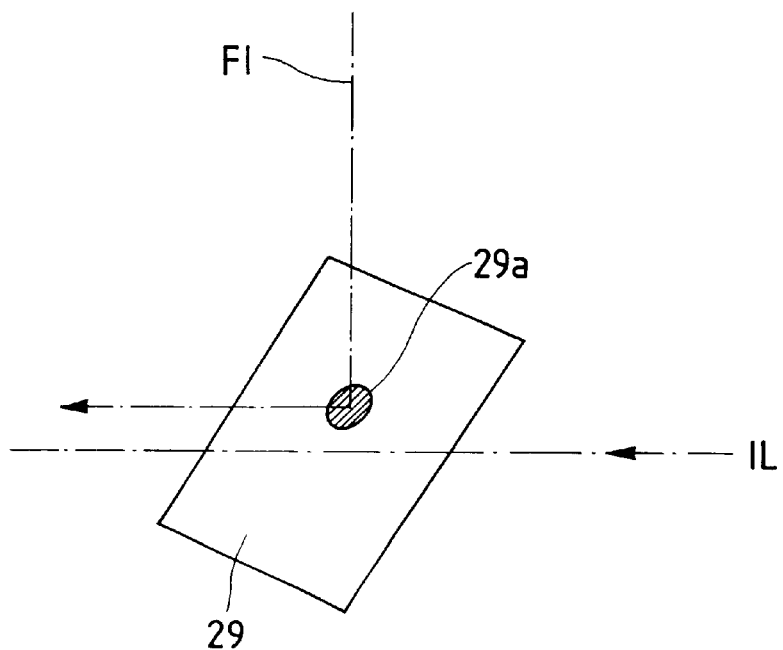
FIG. 4 is a perspective view of a partially reflecting mirror.

The partially reflecting mirror 29 is provided with a small reflecting area 29a in the portion thereof which is slightly eccentric from the optical axis of the illumination optical system, as shown in FIG. 4, and the beam of light FI from the near infrared light source 34 is all reflected by this reflecting area 29a, is made coaxial with the illuminating light IL from the illuminating light source 21 and is projected onto the fundus Ea of the eye E to be examined. At this time, the reflecting area 29a is regulated so as to become substantially conjugate with the fundus Ea of the eye and therefore is formed as a shadow image PR' on the television camera 62, and this image is displayed on the television monitor 64. The examiner effects the focusing of the eye fundus image Ea' while observing the television monitor 64.

When the focus knob 74 is driven, the focusing lens 55 and the focus indicator 33 are moved together along the optical axis. At this time, the probing beam from the laser source 67 for measurement is formed as a spot image PS on the focal plane f lying at a position conjugate with the fundus Ea of the eye by the lens 66, and that conjugate relationship is regulated via the lens 65. When the focusing lens 55 is moved along the optical axis by the focus knob 74, the image pickup surface of the television camera 62, the image pickup surface of the CCD line sensor 72 and the focal plane f of the lens 66 are made conjugate with the fundus Ea of the eye at a time and therefore, the focusing of the eye fundus image Ea' received by the television camera 62, the spot image PS and the blood vessel image Ev' received by the CCD line sensor 72 is performed.

Also, the focus indicator 33 is moved along the optical axis, the reflecting area 29a of the partially reflecting mirror 29 is regulated so as to be disposed at a position conjugate with the fundus Ea of the eye which is between the relay lenses 28 and 30, and the imaged position of the indicator S by the lens 41 is made conjugate with the fundus Ea of the eye and therefore, when the eye fundus image Ea' is focused, the indicator S is made in line at the center of the central image PR' as indicated by an arrow in FIG. 3.

Figure 5:
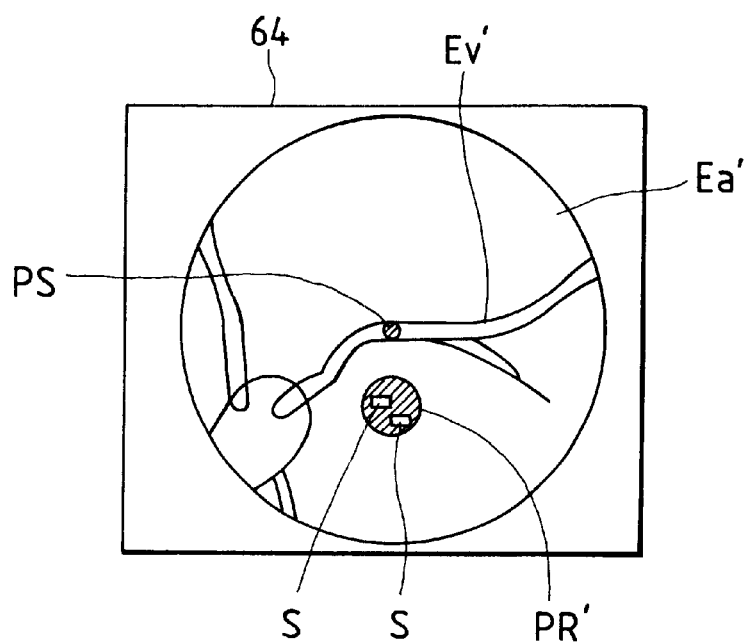
FIG. 5 illustrates the focus indicator with a split image.

When conversely, the eye fundus image Ea' is out of focus, the index mark image S is confirmed as being separated into two parts as shown in FIG. 5. The examiner can know the depth of the blood vessel Ev being measured, from the degree of the deviation between the two index mark images. At this time, in operative association with the focus knob 74, the pin hole 58 in the observation optical system 63 is also moved along the optical axis while keeping its conjugate relationship with the fundus.

Figure 6:
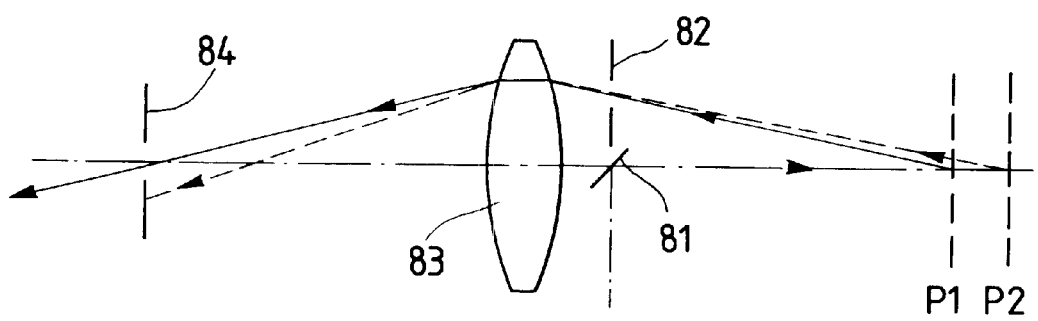
FIG. 6 is a schematic view illustrating the action of a pin hole.

The function of the pin hole 58 will now be described with reference to the schematic view of FIG. 6. In FIG. 6, the position of the blood vessel Ev on the fundus Ea of the eye which is to be measured is represented by a measurement region P1, and the position of the blood vessel Sv in the choroid RC, behind the blood vessel Ev is represented by a measurement region P2. The beam of light from the laser source 67 for measurement enters the mirror 81 from below it, is reflected to right and left and illuminates the measurement region P1. The beam of reflected light on the measurement region P1 which is indicated by solid line passes through an opening 82 which performs the function of determining the light receiving direction equal to that of the pair of small mirrors 53a and 53b, and passes through a pin hole 84, whereafter it is received by a photomultiplier, not shown, because pin hole 84 is made conjugate with the measurement region P1 by a lens 83 (corresponding to the lenses 57a, 57b). In the above-described optical system, the beam of reflected light on the measurement region P2 which is indicated by dotted line, cannot pass through the pin hole 84 and therefore, is not received by the photomultiplier.

As described above, in the present embodiment, with the aid of the pin hole 58, only the beam of reflected light on the blood vessel Ev lying at a particular depth is received by the photomultipliers 59a and 59b, whereby it is possible to measure the velocity of only a desired blood flow. In an actual examination, the examiner effects the setting of the depth of the blood vessel Eb to be measured by means of the focus knob 74 while observing the separated condition of the indicator S on the eye fundus image Ea' displayed on the television monitor 64 shown in FIG. 3, thereby effecting the focusing of the eye fundus image Ea'. After the termination of the focusing, the examiner effects measurement, brings the blood vessel Ev and the spot image PS into coincidence with each other, and selects a region to be measured.

In the examiner's field of view, the spot image PS is fixed at the center of the field of view, and at this time, the eye fundus image is recognized as moving. When the image rotator 32 is then rotated, the eye fundus image Ea' shown in FIG. 3 is rotated about the spot image PS lying at the center of the field of view. The examiner can bring the direction of running of the blood vessel Ev to be measured into coincidence with the direction of an axis A. Here, the direction of the coordinates axis A indicates the direction of the line of intersection between the plane passing through the centers of the pair of small mirrors 53a and 53b and the fundus Ea of the eye E to be examined, and the CCD line sensor 72 enlargedly picks up the image of a bar-like area I.

Bringing the blood vessel Ev to be measured into coincidence with the direction of the axis A as described above is similar to the fact that in equation (2) shown for example of the prior art, $\cos \beta = 1$. As described in the example of the prior art, the principle of velocity detection is obtained from the interference signal between the scattered reflected light from the blood vessel wall and the scattered reflected light in the blood flow and therefore, even if during measurement, the eyeball moves in the direction of the axis A, the result of measurement will not be affected because the blood flow in the blood vessel Ev is substantially parallel to the direction of the axis A. However, if the eyeball moves in a plane orthogonal to the axis A, the measuring laser beam from the laser source 67 for measurement will deviate from the region to be measured on the blood vessel Ev and thus, measurement will become impossible. In the present embodiment, the blood vessel detecting system 68 and the image stabilizer 48 cooperate with each other to effect one-dimensional tracking in the direction of an axis D orthogonal to the axis A.

The CCD line sensor 72 of the blood vessel detecting system 68 picks up the one-dimensional image of the blood vessel image Ev' in the direction of the axis D while the region to be measured is selected by the spot image PS. The amount of one-dimensional movement of the blood vessel image Ev' on the CCD line sensor 72 is calculated from the light reception signal of the CCD line sensor 72 by the controller 73 to thereby make a driving signal for the galvanometric mirror 44 of the image stabilizer 48, and the galvanometric mirror 44 is driven by the driving means 50, whereby the picked-up position of the blood vessel image Ev' by the CCD line sensor 72 is controlled so as to be always constant.

In the present embodiment, the depth of the region to be measured is judged from the degree of separation of the index mark image S displayed on the television monitor 64, but alternatively, for example, the image pickup region on the fundus Ea of the eye by the CCD line sensor 72 can be enlarged with the index mark image S, whereby this index mark image S can be analyzed and quantitatively evaluated, and be displayed as the depth of the region to be measured on the television monitor 64. Also, as in a single-lens reflex camera, a split prism may be provided in the observation optical system 63 to thereby divide the blood vessel image Ev', and the information of the depth of the region to be measured may be obtained from the degree of this division.

In the present embodiment, it is also possible to know the depth of the region to be measured from the contrast of the blood vessel image Ev' picked up by the focus indicator 33 and the CCD line sensor 72. Further, Doppler measurement has been described as an example of the method of detecting the blood flow velocity, whereas this detecting method is not restrictive, but the present invention is applicable to any velocity measuring method in which the direction of incidence of the beam of measuring light onto a particular area of the fundus Ea of the eye E to be examined and the direction of reception of the beam of reflected light on the fundus Ea of the eye differ from each other.

What is claimed is:

1. A retinal blood flow measuring apparatus comprising:
an irradiation system for spot-applying a laser beam for measurement onto a blood flow in a fundus of an eye to be examined;
a light receiving device for receiving the reflected light of the laser beam for measurement from the fundus of the eye, the blood flow condition of the fundus of the eye being measured from an output signal of said light receiving device; and
a prescribing member for prescribing the position of the reflected light from the fundus of the eye in the direction of depth of the fundus of the eye,
wherein said prescribing member has first light beam limiting means disposed at a position between the eye to be examined and said light receiving device which is conjugate with the pupil of the eye to be examined and which is eccentric relative to the position of the laser beam for measurement on the pupil of the eye to be examined, and second light beam limiting means disposed at a position conjugate with the fundus of the eve to be examined.

2. The apparatus of claim 1, wherein said prescribing member prescribes the directions of the beam of incident light onto a region to be measured on the fundus of the eye and the beam of emergent light from said region to be measured, and the portion of intersection between said beam of incident light and said beam of emergent light is specified as the region to be measured.

3. An apparatus according to claim 1, wherein said irradiation system, said light receiving device and said prescribing member constitute a measuring system;

said apparatus further comprising an observing system having a focus adjustment function and for observing the fundus of and eye to be examined, provided separately from said measuring system; and wherein said second light beam limiting means operates together with the focus adjustment function of said observing system to vary a position in an optical axis direction thereof, so that a position in the direction of depth of a portion to be measured by said measuring system is capable of being determined while being observed by said observing system.

4. The apparatus of claim 1, wherein said prescribing member further has third light beam limiting means disposed in the optical path of the laser beam for measurement in said irradiation system.

5. The apparatus of claim 4, wherein said first light beam limiting means and said third light beam limiting means are imaged at different positions on the pupil.

6. The apparatus of claim 1, wherein said laser beam for measurement is infrared light.

7. The apparatus of claim 1, further comprising display means for displaying the position of the region to be measured in the direction of depth at the fundus of the eye.

8. The apparatus of claim 7, wherein said display means displays a focus indicator.

9. The apparatus of claim 1, wherein the optical path of said irradiation system and the optical path from the eye to be examined to said light receiving device pass through a common optical system.

10. The apparatus of claim 9, wherein said common optical system has an image rotator.

11. The apparatus of claim 1, further comprising a monitor for observing the fundus of the eye to be examined.

12. The apparatus of claim 11, further having illuminating means for observation discretely from said irradiation system.

13. The apparatus of claim 12, wherein the illuminating light of said illuminating means for observation is near infrared light.

14. The apparatus of claim 1, further comprising movement detecting means for detecting the movement of the fundus of the eye to be examined, and means for displacing an optical path on the basis of said movement detecting means.

15. A retinal blood flow measuring apparatus comprising:

an irradiation system for spot-applying a laser beam for measurement onto a blood flow in a fundus of an eye to be examined;

a light receiving device for receiving the reflected light of the laser beam for measurement from the fundus of the eye, the blood flow condition of the fundus of the eye being measured from an output signal of said light receiving device;

specifying members for specifying the portion of the region of the eye to be measured in the direction of depth of the fundus of the eye; and an observation system for observing a retinal image of the eye including the region of the eye to be measured; and an indication system for indicating positional information of the region of the eye to be measured along a focusing direction of said observation system.

16. The apparatus of claim 15, wherein said observation system comprises a monitor for observing the fundus of the eye to be examined.

17. The apparatus of claim 16, further having illuminating means for observation discretely from said irradiation system.

18. The apparatus of claim 17, wherein the illuminating light of said illuminating means for observation is near infrared light.

19. The apparatus of claim 15, further comprising movement detecting means for detecting the movement of the fundus of the eye to be examined, and means for displacing an optical path on the basis of said movement detecting means.

* * * * *

UNITED STATES PATENT AND TRADEMARK OFFICE
CERTIFICATE OF CORRECTION

PATENT NO. : 6,607,272 B1
DATED : August 19, 2003
INVENTOR(S) : Shinya Tanaka

It is certified that error appears in the above-identified patent and that said Letters Patent is hereby corrected as shown below:

Title page,
Item [56], References Cited, U.S. PATENT DOCUMENTS, insert the following:

| | | | |
|---|---|---|---|
| -- 5,177,511 | 01/1993 | Feuerstein et al. | 351/205 |
| 5,106,184 | 04/1992 | Milbocker | 351/221 |
| 5,090,799 | 02/1992 | Makino et al. | 351/221 |
| 4,346,991 | 08/1982 | Gardner et al. | 356/28.5 --. |

OTHER PUBLICATIONS, insert the following:

-- Feke, et al., Laser Doppler Technique for Absolute Measurement of Blood Speed in Retinal Vessels, IEEE Transactions on Biomedical Engineering, Vol. BME-34, No. 9, September 1987, pp. 673-680 --.

Column 4,
Line 28, "probing" should read -- a probing --.

Column 5,
Line 36, "angle a" should read -- angle $a$ --.

Column 8,
Line 56, "eve" should read -- eye --.

Signed and Sealed this

Twenty-third Day of December, 2003

JAMES E. ROGAN
*Director of the United States Patent and Trademark Office*